(12) United States Patent
Cadossi et al.

(10) Patent No.: US 10,376,707 B2
(45) Date of Patent: Aug. 13, 2019

(54) METHOD FOR THE TREATMENT OF ISCHEMIC STROKE BY APPLYING AN ELECTROMAGNETIC FIELD

(71) Applicant: IGEA S.p.A., Carpi (IT)

(72) Inventors: Ruggero Cadossi, Carpi (IT); Donata Marazzi, Carpi (IT)

(73) Assignee: IGEA S.p.A., Carpi (IT)

(*) Notice: Subject to any disclaimer, the term of this patent is extended or adjusted under 35 U.S.C. 154(b) by 385 days.

(21) Appl. No.: 14/657,365

(22) Filed: Mar. 13, 2015

(65) Prior Publication Data

US 2015/0258346 A1 Sep. 17, 2015

Related U.S. Application Data

(60) Provisional application No. 61/953,447, filed on Mar. 14, 2014.

(51) Int. Cl.
| | |
|---|---|
| *A61N 2/02* | (2006.01) |
| *A61N 2/00* | (2006.01) |
| *A61N 2/04* | (2006.01) |
| *A61N 1/40* | (2006.01) |

(52) U.S. Cl.
CPC .............. *A61N 2/004* (2013.01); *A61N 2/02* (2013.01); *A61N 1/40* (2013.01); *A61N 2/006* (2013.01)

(58) Field of Classification Search
CPC . A61N 2/12; A61N 2/00; A61N 2/002; A61N 2/004; A61N 2/006; A61N 2/008; A61N 2/02
See application file for complete search history.

(56) References Cited

U.S. PATENT DOCUMENTS

| 7,566,295 | B2 | 7/2009 | Giardino et al. | |
|---|---|---|---|---|
| 2007/0083245 | A1* | 4/2007 | Lamensdorf | A61N 1/36082 607/45 |
| 2007/0173889 | A1* | 7/2007 | Rosenspire | A61N 1/32 607/2 |
| 2008/0103350 | A1* | 5/2008 | Farone | A61N 2/006 600/13 |
| 2010/0094384 | A1* | 4/2010 | De Taboada | A61N 5/0613 607/88 |
| 2012/0116149 | A1* | 5/2012 | Pilla | A61N 1/36025 600/14 |
| 2014/0194726 | A1* | 7/2014 | Mishelevich | A61N 7/00 600/411 |

(Continued)

OTHER PUBLICATIONS

De Mattei, et al. "Adenosine analogs and electromagnetic fields inhibit prostaglandin $E_2$ release in bovine synovial fibroblasts," Osteoarthritis and Cartilage 17:252-262 (2009).

(Continued)

*Primary Examiner* — Carrie R Dorna
(74) *Attorney, Agent, or Firm* — Marshall, Gerstein & Borun LLP

(57) ABSTRACT

There is disclosed a method for the treatment of cerebral ischemic stroke in a subject in need thereof comprising the steps of (a) identifying an ischemic area of the brain of the subject; and (b) applying an effective electromagnetic field to the ischemic area of the brain, wherein the electromagnetic field is effective to reduce local edema, to increase neuronal survival and/or reduce neuronal apoptosis.

7 Claims, 11 Drawing Sheets

(56) References Cited

U.S. PATENT DOCUMENTS

2014/0303425 A1* 10/2014 Pilla .................. A61N 2/006
                                                      600/14

OTHER PUBLICATIONS

Varani, et al. "Effect of low frequency electromagnetic fields on A2A adenosine receptors in human neutrophils," British Journal of Pharmacology 136:57-66 (2002).
Varani, et al. "Characterization of adenosine receptors in bovine chondrocytes and fibroblast-like synoviocytes exposed to low frequency low energy pulsed electromagnetic fields," Osteoarthritis and Cartilate 16:292-304 (2008).
Varani, et al. "Alteration of $A_3$ adenosine receptors in human neutrophils and low frequency electromagnetic fields," Biochemical Pharmacology 66:1897-1906 (2003).
Vincenzi, et al. "The Anti-Tumor Effect of $A_3$ Adenosine Receptors is Potentiated by Pulsed Electromagnetic Fields in Cultured Neural Cancer Cells," PLoS ONE, 7(6):1-14 (2012).
Grant et al., "Protection Against Focal Cerebral Ischemia Following Exposure to a Pulsed Electromagnetic Field," Bioelectromagnetics 15:205-216 (1994).

* cited by examiner

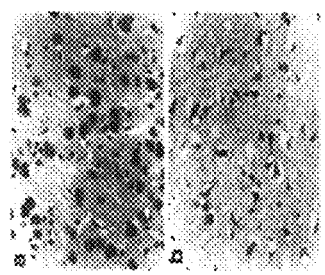
FIG. 3A
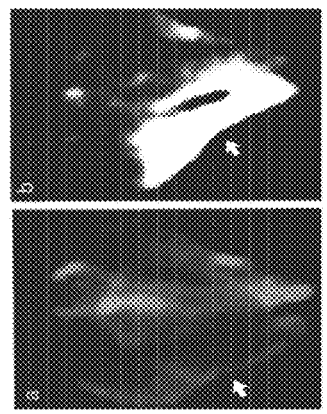
FIG. 3B
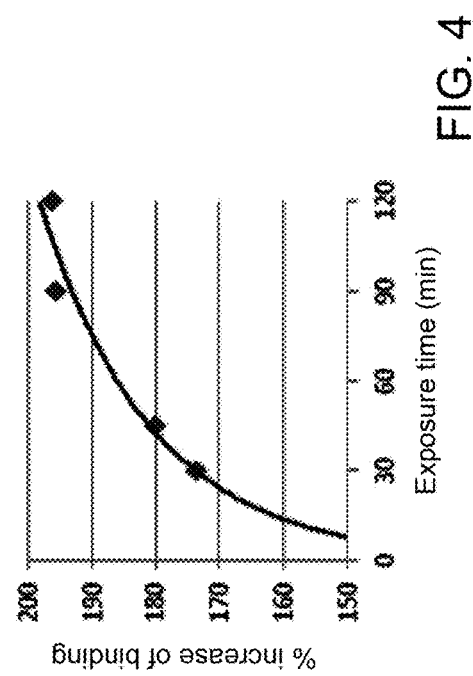
FIG. 4
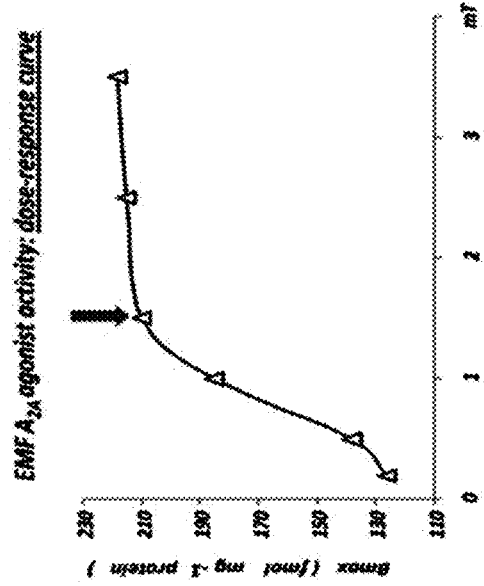

Note: *, P<0.01 vs normoxia, **, P<0.01 vs hypoxia.

Note: *, P<0.01 vs normoxia, **, P<0.01 vs hypoxia.

Note: *, $P<0.01$ vs control.

Note: *, P<0.01 vs normoxia; **, P<0.01 vs hypoxia or hypoxia + LPS.

METHOD FOR THE TREATMENT OF ISCHEMIC STROKE BY APPLYING AN ELECTROMAGNETIC FIELD

CROSS-REFERENCE TO RELATED APPLICATIONS

This application claims the priority benefit under 35 U.S.C. § 119(e) of Provisional U.S. Patent Application No. 61/953,447, filed Mar. 14, 2014, the disclosure of which is incorporated herein by reference in its entirety.

SUMMARY

The present invention relates to a method for the treatment of cerebral ischemic stroke in a subject in need thereof.

Stroke is the third leading cause of death in the United States. More than 140,000 people die each year from stroke in the United States. Moreover, stroke is the leading cause of serious, long-term disability in the United States. Each year, approximately 795,000 people suffer a stroke: about 600,000 of these are first attacks, and 185,000 are recurrent attacks.

Stroke costs the United States an estimated $36.5 billion each year. This total includes the cost of health care services, medications to treat stroke, and missed days of work. Indirect costs continuously increase with aging of the population.

Currently, research for the treatment of ischemic stroke is exclusively directed to pharmacological therapy. Thrombolysis through tissue plasminogen activator (rt-PA) is the only acute phase therapy that has been shown effective in modifying the course of disease in view of acceptable side effects. Its use is however limited to cases that reach a specialized hospital within a few hours from the stroke and in which there are no bleeding disorders. This results in 90% of stroke patients not receiving adequate treatment. Moreover, rt-PA is only effective to partially restore perfusion in the ischemic penumbra (the borderline ischemic tissue area surrounding the central ischemic core, which undergoes necrosis) and prevent further damage to this area, thus limiting neurological deficit. Rt-PA, however, does not act on the central ischemic core, the necrosis of which has up to now been considered to be irreversible. Further, the release of active substances from the necrotic brain tissue causes cerebral edema, which cannot be counteracted pharmacologically and represents a very dangerous development of ischemic stroke.

In recent years, several clinical trials have been launched to test the effectiveness of neuroprotective drugs. However, none of these clinical trials have confirmed results obtained in vitro or in an animal model.

The need is therefore strongly felt to develop new alternatives to rt-PA treatment for stroke patients, in particular treatments that have an effect in reducing local edema of the penumbra, in increasing neuronal survival and/or in reducing neuronal apoptosis in the central necrotic ischemic area.

U.S. Pat. No. 7,566,295B2 in the name of the same applicant discloses an electromagnetic field stimulator device and a method for preserving the integrity of articular cartilage subject to degeneration by applying an electromagnetic field generated by the device to cartilaginous tissue. The device of U.S. Pat. No. 7,566,295B2 allows the generation of a predefined electromagnetic field to be applied at a predetermined depth of the body of a mammal.

However, the device does not allow to target the magnetic field to a certain injured area of the body, which can be located at different depths and be of different sizes depending on the subject.

In particular, in brain stroke, the injured area may be located in different areas of the head, at different depths and involve more or less widespread areas including different types and numbers of cells. Moreover, the device of U.S. Pat. No. 7,566,295B2 does not allow to specifically target cerebral tissue.

In view of the above, it is an object of the present invention to provide a method for the treatment of cerebral ischemic stroke which is effective in reducing neuronal degeneration and improving recovery of damaged brain tissue, and can be applied to patients having a different extent and position of brain damage.

BRIEF DESCRIPTION OF THE DRAWINGS

FIG. 3A shows nuclear magnetic resonance images of brain ischemia in rabbits treated with electromagnetic fields (left) versus untreated (right);

FIG. 3B shows coronal histological sections of brain ischemia in rabbits treated with electromagnetic fields (top) versus untreated (bottom);

FIG. 4 shows activity of electromagnetic fields on the $A_{2A}$ receptor as a function of the peak value of the magnetic field (left) and of the exposure time (right);

DESCRIPTION OF THE INVENTION

Figure 1:
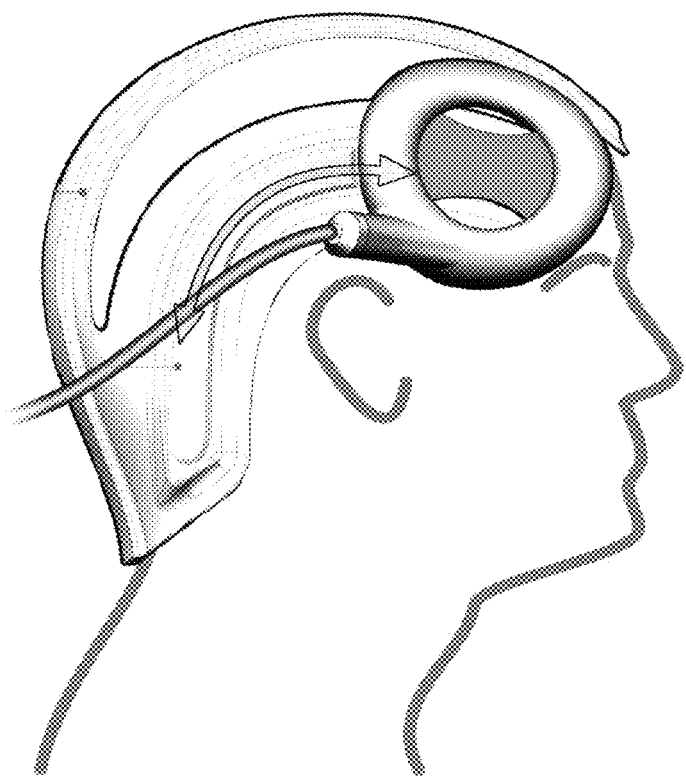
FIG. 1 shows an example of a headset for wearing a solenoid which generates an electromagnetic field to carry out the method according to the invention.
Figure 2:
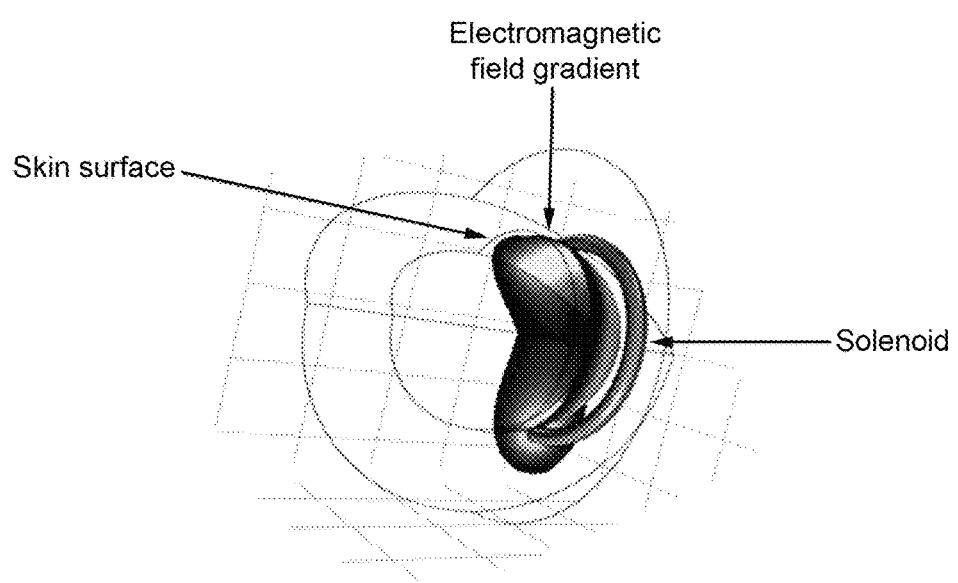
FIG. 2 shows an example of the 3D modeling of the electromagnetic field gradient.
Figure 5:
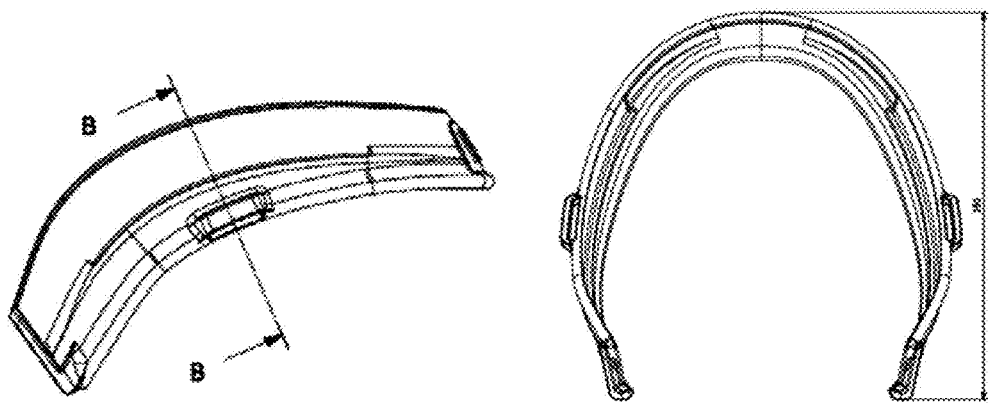
FIG. 5 shows another example of the headset for wearing a solenoid which generates an electromagnetic field to carry out the method according to the invention.
Figure 6:
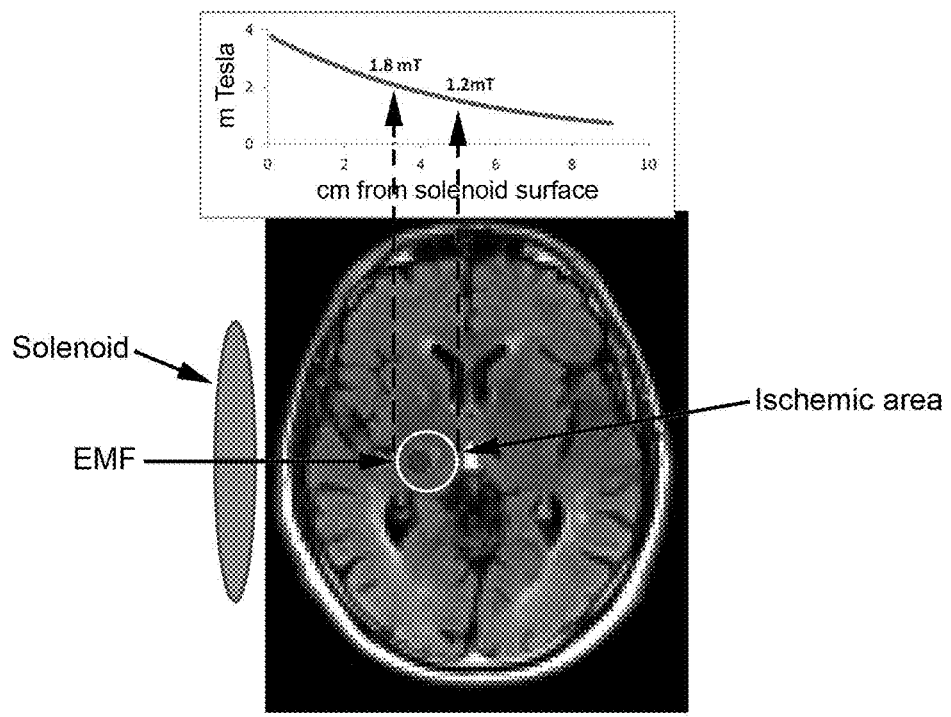
FIG. 6 shows an image of the identification of the ischemic area (white circle), the determination of the depth of the ischemic area and the simulation of the electromagnetic field values on the basis of the selected solenoid and the check that the ischemic area is exposed to values in the range from 1.2 to 1.8 mTesla (arrows); EMF=electromagnetic field.
Figure 7:
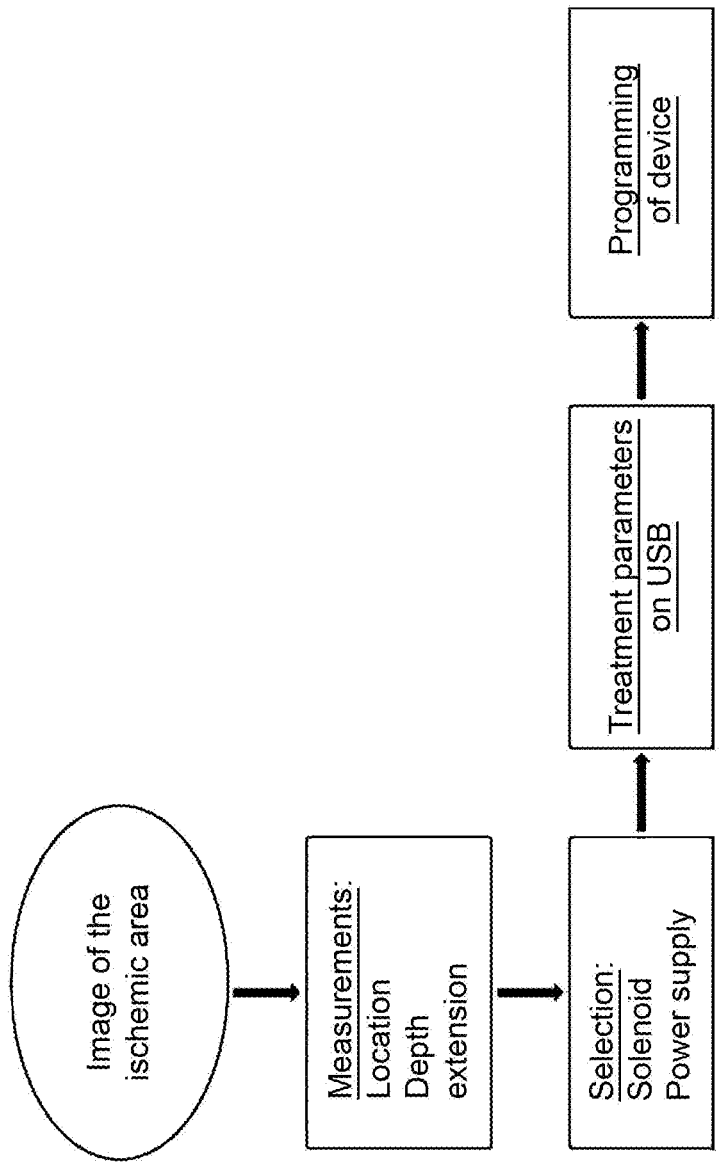
FIG. 7 shows a diagram of the steps of the procedure for identifying the treatment parameters and the export thereof to the device for carrying out the method of the invention.
Figure 8:
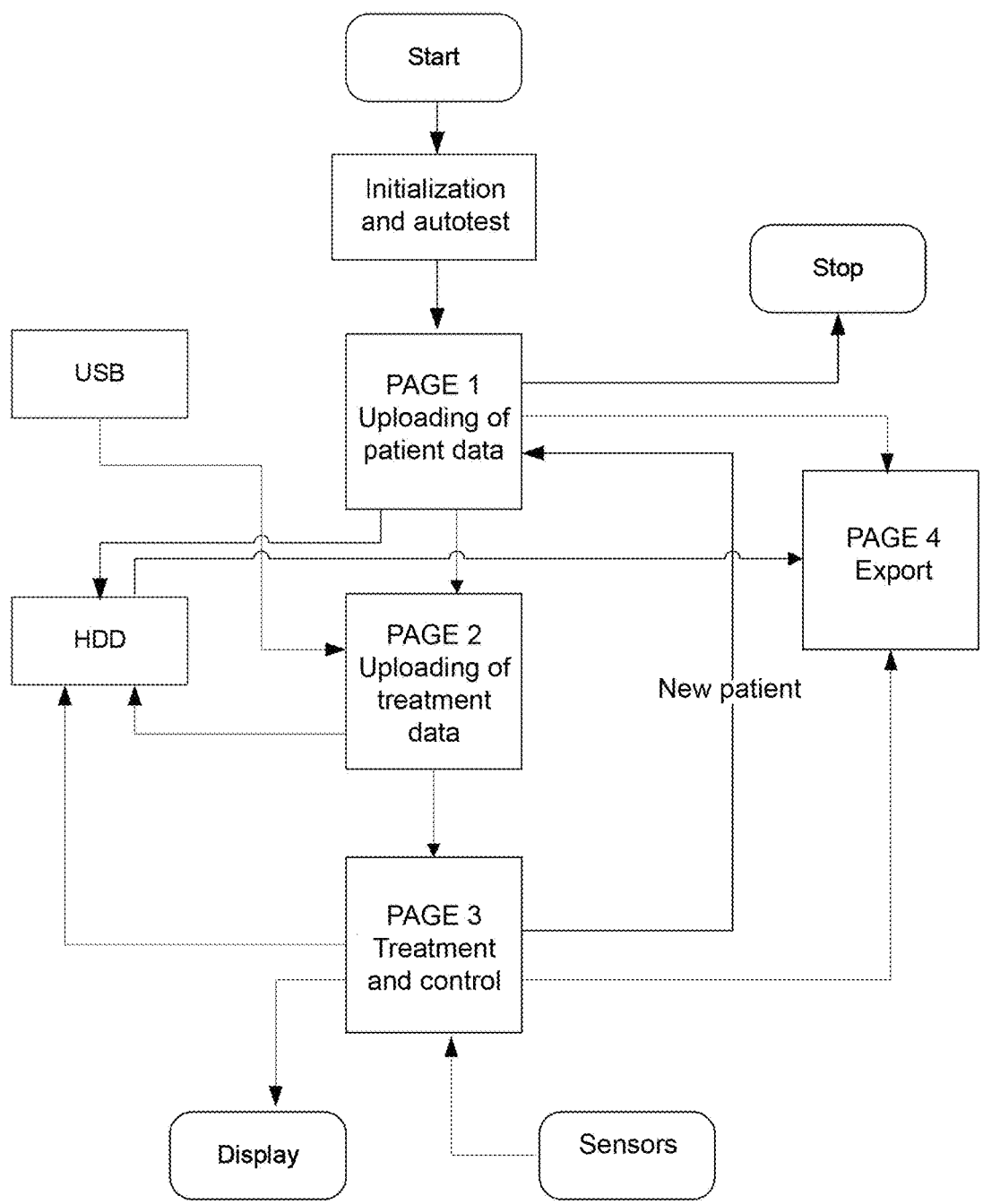
FIG. 8 shows a diagram of the operation of the software of the device.

The method for the treatment of cerebral ischemic stroke in a subject, preferably a human, in need thereof according to the invention comprises the steps of:

(a) identifying an ischemic area of the brain of the subject; and (b) applying an effective electromagnetic field to the ischemic area of the brain, wherein the electromagnetic field is effective to reduce local edema, to increase neuronal survival and/or reduce neuronal apoptosis.

Neuronal apoptosis is reduced through modulation of expression of the HIF-1α gene.

The cerebral ischemic stroke can be an ischemic or a hemorrhagic stroke.

Treatment with an effective electromagnetic field should be carried out during the acute phase of the ischemic stroke, i.e. during the first days following the stroke, in particular from 1 to 48 hours, preferably 12 to 36 hours, more preferably from about 24 hours after the occurrence of the cerebral ischemic stroke and for the following 3 to 10 days, preferably for the following 4 to 6 days, more preferably for the following 5 days.

The ischemic area is preferably identified by nuclear magnetic resonance (NMR) or computed axial tomography (CAT). Parameters such as depth and extension of the ischemic area are used by a software to compute and set the parameters for generating the effective electromagnetic field at the injured area.

The electromagnetic field applied to the ischemic area of the brain preferably has a value from 1 to 3 mTesla, more preferably a value from 1.2 to 1.8 mTesla.

The electromagnetic field is preferably applied for a time from 1 hour to 4 hours. More preferably the electromagnetic field is applied for about 2 hours. This is because, after about 2 hours, the therapeutic effect reaches a maximum value which remains constant for longer treatments. On the other side, treatments longer than 2 hours are too stressful for patients, which become uncomfortable and nervous.

In another aspect, the disclosure provides a method for the treatment of cerebral ischemic stroke in a subject in need thereof comprising the steps of: (a) identifying an ischemic area of the brain of the subject; and (b) applying an effective electromagnetic field to the ischemic area of the brain, wherein the electromagnetic field is effective to reduce local edema, to increase neuronal survival or to reduce neuronal apoptosis, relative to a subject that has suffered a stroke but to whom the effective electromagnetic field was not applied. In some embodiments, neuronal apoptosis is reduced through modulation of expression of the HIF-1α gene.

In some embodiments, in step (a), the ischemic area is identified by nuclear magnetic resonance or computed axial tomography. In further embodiments, in step (b), the electromagnetic field applied to the ischemic area of the brain has a value from 1 to 3 mTesla. In some embodiments, in step (b), the electromagnetic field applied to the ischemic area of the brain has a value from 1.2 to 1.8 mTesla. In still further embodiments, in step (b), the electromagnetic field is applied to the ischemic area of the brain for a time from 1 hour to 4 hours for 3 to 10 days starting from 1 to 48 hours after the occurrence of the cerebral ischemic stroke.

In some embodiments, in step (b), the electromagnetic field is applied to the ischemic area of the brain for a time from 1 hour to 4 hours for 4 to 6 days starting from 12 to 36 hours after the occurrence of the cerebral ischemic stroke.

In some embodiments, in step (b), the electromagnetic field is applied to the ischemic area of the brain for a time from 1 hour to 4 hours for 5 days starting from 24 hours after the occurrence of the cerebral ischemic stroke.

In additional embodiments, in step (b), the electromagnetic field is applied to the ischemic area of the brain for a time of about 2 hours for 5 days starting from about 24 hours after the occurrence of the cerebral ischemic stroke.

The disclosure also contemplates, in various embodiments, that the subject is a mammal. In further embodiments, the subject is human.

The device for applying the electromagnetic field comprises a solenoid which can be worn on a headset made of 2 mm-thick thermoformed acrylonitrile butadiene styrene (ABS) and carrying a Velcro strip to move the solenoid forward and backward (FIG. 1). In certain cases, different kinds of solenoids, even inductively coupled solenoids, may be chosen on the basis of the data obtained through NMR or CAT.

The device does not have to be used by technically qualified staff as it can automatically compute the settings and parameters necessary for directing the effective electromagnetic field to the injured area.

The device comprises a microprocessor board with a TFT touch screen display and a USB interface. A dedicated software generates the treatment parameters on the basis of data inputted via a USB stick or directly through the touch screen. The parameters are used to drive the selected solenoid so as to maintain effective values of treatment independently of the depth of the injured areas.

Two different modes can be used based respectively on current control and on voltage control for the generation of a magnetic field. The first mode provides that the impulse is generated by increasing current in a linear manner and for the whole duration of the impulse (1.3 ms). The second mode exploits the high impedance of the solenoid, and thus the applied voltage, to obtain a constant variation of the magnetic field for the whole duration of the pulse (1.3 ms). In the first case, the solenoids are light and have a low number of coils, whereas in the second case the solenoids will be much heavier and with a number of coils as high as 1000 and above.

The interface software allows to display the patient's data, the treatment data, the parameters and the shape of the signal employed, the count-down of the time remaining for the daily treatment, and export all the data to other supports.

EXAMPLES

Preclinical trials have shown that the application of electromagnetic fields from 1 to 3 mTesla to areas of the brain affected by stroke represents an effective strategy for neuroprotection and an alternative to pharmacological treatment.

In particular, a study performed on a model of brain ischemia in rabbits, showed that exposure to electromagnetic fields from 1 to 3 mTesla determined a considerable and significant decrease (65%-70%) of the ischemic area (evaluated by magnetic resonance). Furthermore, the animals showed an early recovery of the action potential generated in neurons and a greater survival of neurons in the ischemic area (FIG. 4).

Electromagnetic fields have been shown to act on neuronal cells by modifying gene expression, promoting the growth of neurites and reducing apoptosis.

Research carried out at the University of Ferrara has identified the adenosine $A_{2A}$ receptor as an important cell target of electromagnetic fields. The effect of electromagnetic fields on the adenosine $A_{2A}$ receptor is associated to strong anti-inflammatory effect which in combination explain the results obtained on the brain stroke animal model. In vitro agonist activity at the adenosine A2A receptor is obtained for values of electromagnetic field higher than 1 mTesla and for exposure times of at least 20 minutes (FIG. 4).

The effect of PEMFs on cell viability in normoxic or hypoxic condition was evaluated. To investigate the cellular mechanism of PEMFs the HIF-1α gene activation was studied in normoxic or hypoxic conditions.

Cell Cultures.

SHSY-5Y cells derived from neuroblastoma and purchased from the American Type Culture Collection (Manassas, Va., USA) and PC 12 rat pheochromocytoma cells also purchased from the American Type Culture Collection (Manassas, Va., USA) were used. SHSY-5Y were cultured in DMEM F12 medium (Invitrogen, Grand Island, N.Y., USA) supplemented with 10% FBS (Thermo Scientific, Waltham, Mass., USA) and the cultures were maintained at 37° C. in a humidified atmosphere with 5% CO2. PC12 cells were purchased from American Type Culture Collection (Manassas, Va., USA) and were maintained in DMEM F12 medium supplemented with 5% FBS, 10% horse serum, L-glutamine (2 mM), penicillin (100 U/ml) and streptomycin (100 μg/ml) in a humidified atmosphere (5% CO2) at 37° C. Cells were subcultured three times a week at a density of 500000/ml and the differentiation was achieved by treatment with 50 ng/ml nerve growth factor (NGF, Sigma, St Louis, Mo.) for one week (Vincenzi et al., 2012).

Electromagnetic Field Exposure System

The cells were exposed to PEMFs generated by a pair of rectangular horizontal coils (14 cm×23 cm), each made of 1400 turns of copper wire placed opposite to each other. The culture was placed between this pair of coils so that the plane of the coils was perpendicular to the culture flasks. The coils were powered by the PEMF generator system (IGEA, Carpi, Italy) used in previous studies (Varani et al., 2002, 2003, 2008; De Mattei et al., 2009; Vincenzi et al., 2012), which produced a pulsed signal with the following parameters: pulse duration of 1.3 ms and frequency of 75 Hz, yielding a 0.1 duty cycle. The peak intensity of the magnetic field and peak intensity of the induced electric voltage were detected in air between two coils from one side to the other, at the level of the culture flasks. The peak values measured between two coils in air had a maximum variation of 1% in the whole area in which the culture flasks were placed. The dimensions of the flasks were 9.2 cm×8.2 cm with 10 ml of medium. The peak intensity of the magnetic field was 1.5±0.2 mT and it was detected using the Hall probe (HTD61-0608-05-T, F. W. Bell, Sypris Solutions, Louisville, Ky.) of a gaussmeter (DG500, Laboratorio Elettrofisico, Milan, Italy) with a reading sensitivity of 0.2%. The corresponding peak amplitude of the induced electric voltage was 2.0±0.5 mV. It was detected using a standard coil probe (50 turns, 0.5 cm internal diameter of the coil probe, 0.2 mm copper diameter) and the temporal pattern of the signal was displayed using a digital oscilloscope (Le Croy, Chestnut Ridge, N.Y.). The shape of the induced electric voltage and its impulse length were kept constant.

HIF-1α Analysis

For HIF-1α detection, the cells were put under normoxia or hypoxia. Nuclear extracts from the PC12 cells were obtained by using a nuclear extract kit (Abcam) according to the manufacturer instructions. HIF-1α activation was evaluated by using HIF-1α Transcription Factor Assay (Abcam). HIF-1α specifically binds to the immobilized double stranded DNA (dsDNA) sequence containing the HIF-1α response element (5'-ACGTG-3'). The HIF-1α transcription factor complex is detected by addition of a specific primary antibody. A horseradish peroxidase (HRP)-conjugated secondary antibody is added to provide a sensitive colorimetric readout that was quantified by spectrophotometry at 450 nm wavelength.

Analysis of Cell Viability

Cell viability is an important component of any in vitro cell based assay because culture conditions and experimental treatments can affect cell viability by directly or indirectly inducing cytotoxicity, apoptosis and/or necrosis. A hallmark of viable cells is an intact plasma membrane and intracellular enzymatic activity that form the basis of the Live/Dead cell assay. Live cells are identified on the basis of intracellular esterase activity (generating green fluorescence) and exclusion of the red dye. Dead cells are identified by the lack esterase activity and non-intact plasma membrane which allows red dye staining. Cell viability was analysed by using a Nikon fluorescent microscope (Eclipse 50i).

Figure 9A:
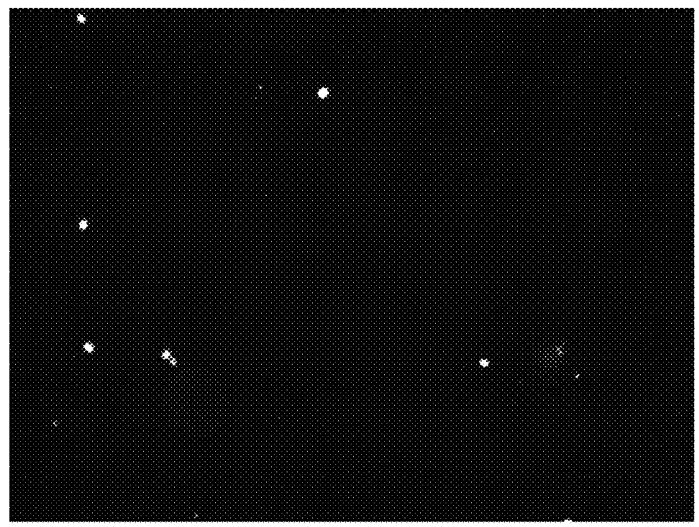
FIG. 9A shows a microphotograph of PC12 cells after 24 hours of incubation in normoxia conditions.
Figure 9B:
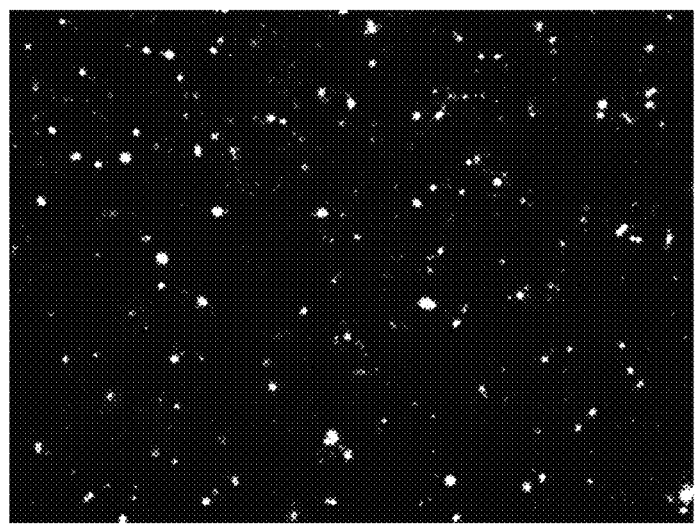
FIG. 9B shows a microphotograph of PC12 cells after 24 hours of incubation in hypoxia conditions.
Figure 9C:
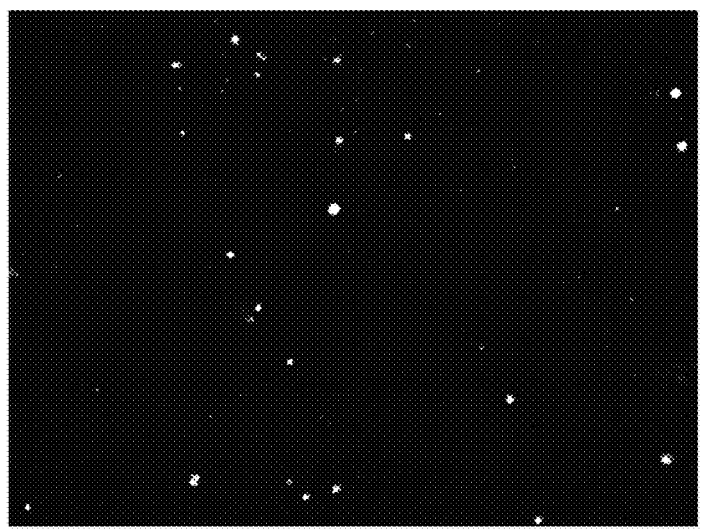
FIG. 9C shows a microphotograph of PC12 cells after hours of incubation in hypoxia conditions in the presence of PEMFs.
Figure 10:
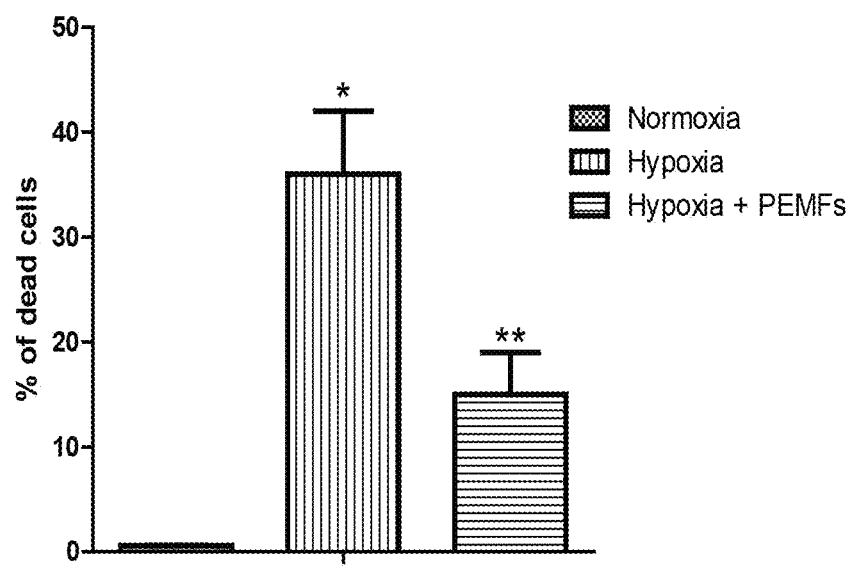
FIG. 10 shows a histogram with results of the live/dead assay performed on PC12 cells after 24 hours of incubation in normoxia, hypoxia and hypoxia in the presence of PEMFs.

FIG. 9A-9C shows representative microphotographs of PC 12 cells respectively after 24 hours of incubation in normoxia (FIG. 9A), hypoxia (FIG. 9B) and hypoxia in the presence of PEMFs (FIG. 9C) where dead cells are stained in red (visible in light grey in the Figures). To verify a possible surviving effect of PEMFs on neuronal damage induced by hypoxia, PC 12 cells were exposed to hypoxia (1% $O_2$) for 24 hours in the absence or in the presence of PEMFs. The viability of PC12 cells was evaluated with fluorescence microscopy and dead or damaged cells were identified by red staining. As reported in FIG. 9A-9C, the treatment of hypoxia for 24 hours significantly increased the number of dead cells respect to normoxia conditions. Interestingly, the presence of PEMFs greatly reduced cell death induced by hypoxia as indicated by the lower number of red stained cells respect to hypoxia condition in the absence of PEMFs (FIG. 9A-9C). The histogram relative to the percentage of dead cells in normoxia, hypoxia and hypoxia in the presence of PEMFs is reported in FIG. 10.

Figure 11A:
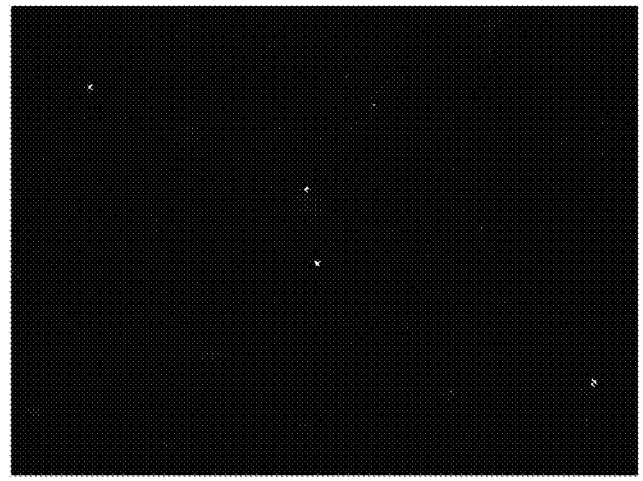
FIG. 11A shows a microphotograph of SHSY-5Y cells after 24 hours of incubation in normoxia conditions.
Figure 11B:
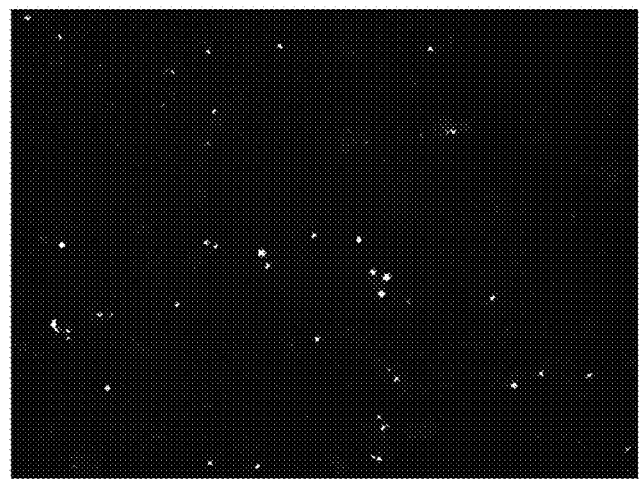
FIG. 11B shows a microphotograph of SHSY-5Y cells after 24 hours of incubation in hypoxia conditions.
Figure 11C:
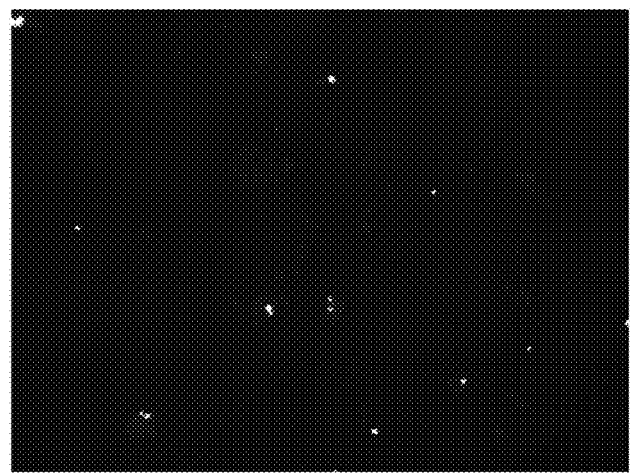
FIG. 11C shows a microphotograph of SHSY-5Y cells after 24 hours of incubation in hypoxia conditions in the presence of PEMFs.
Figure 12:
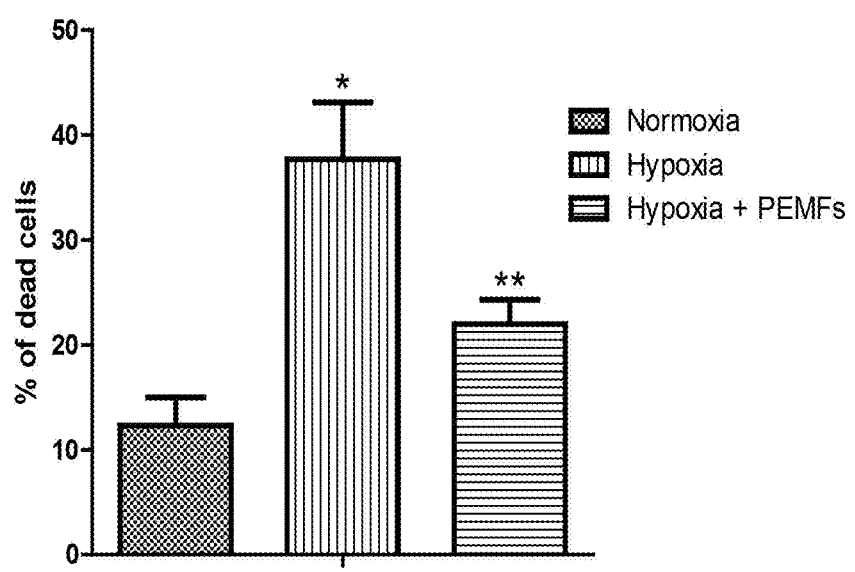
FIG. 12 shows a histogram with results of the live/dead assay performed on SHSY-5Y cells after 24 hours of incubation in normoxia, hypoxia and hypoxia in the presence of PEMFs.

Analogously, FIGS. 11A-11C shows a representative microphotograph of SHSY-5Y cells after 24 hours of incubation in normoxia (FIG. 11A), hypoxia (FIG. 11B) and hypoxia in the presence of PEMFs (FIG. 11C) where dead cells are stained in red (visible in light grey in the Figures). The hypoxia treatment for 24 hours significantly increased the number of dead cells with respect to normoxia conditions whilst the presence of PEMFs greatly reduced cell death induced by hypoxia as indicated by the lower number of red stained cells respect to hypoxia condition in the absence of PEMFs (FIGS. 11A-11C). Moreover, FIG. 12 reports the histogram relative to the percentage of dead cells in normoxia, hypoxia and hypoxia in the presence of PEMFs that is able to mediate a significant effect in the reduction of dead cells.

Figure 13A:
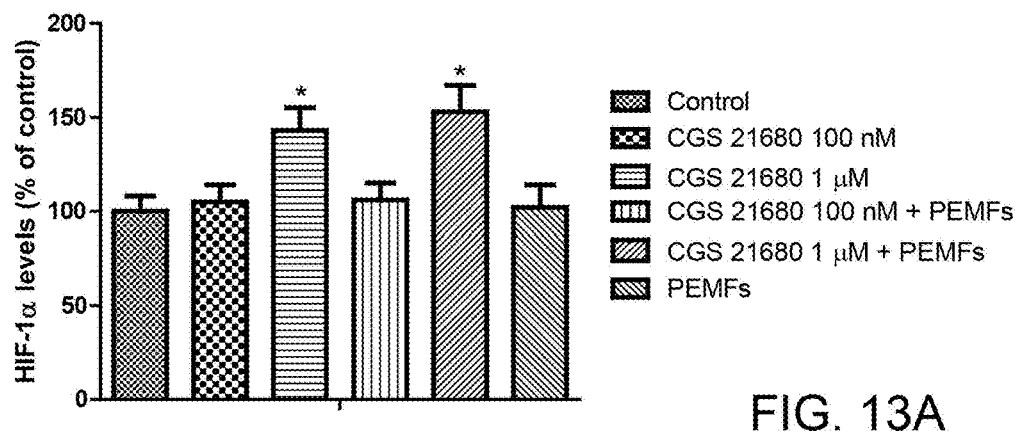
FIG. 13A shows a histogram with results relating to HIF-1α activation in PC12 cells after 2 hours of incubation with the $A_{2A}AR$ agonist CGS 21680 (100 nM or 1 μM), PEMFs or their combination.
Figure 13B:
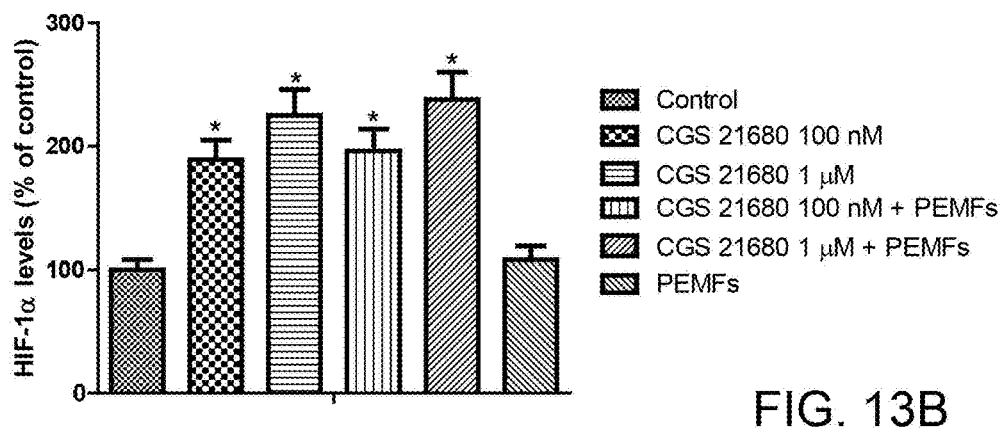
FIG. 13B shows a histogram with results relating to HIF-1α activation in PC12 cells after 6 hours of incubation with the $A_{2A}AR$ agonist CGS 21680 (100 nM or 1 μM), PEMFs or their combination.
Figure 13C:
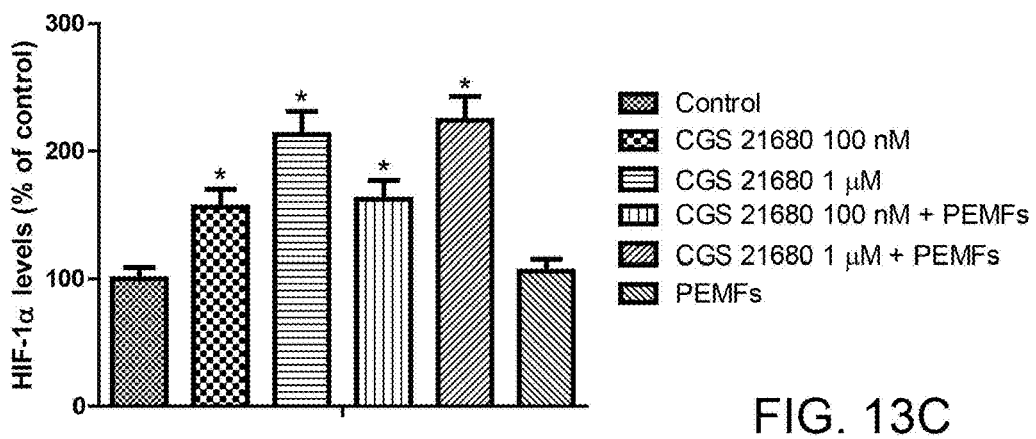
FIG. 13C shows a histogram with results relating to HIF-1α activation in PC12 cells after 24 hours of incubation with the $A_{2A}AR$ agonist CGS 21680 (100 nM or 1 μM), PEMFs or their combination.

To investigate the mechanism of action of PEMFs in the surviving of neuronal cells, the modulation of the transcription factor HIF-1α was investigated. HIF-1α is a key regulator in hypoxia and it has been suggested to be an important player in neurological outcomes following ischemic stroke due to the functions of its downstream genes. In normoxic condition, the treatment of PC12 cells with the $A_{2A}AR$ agonist CGS 21680, PEMFs or their combination for 2, 6 or 24 hours was evaluated on HIF-1α accumulation in nuclear extract (FIGS. 13A-13C). After 2 hours of treatment, CGS 21680 at the 1 μM concentration was able to significantly increase the levels of HIF-1α by 43% with respect to control conditions (FIG. 13A). A more evident effect of the $A_{2A}AR$ agonist was observed after 6 or 24 hours of treatment (FIGS. 13B and 13C). PEMFs exposure did not modulate HIF-1α activation in normoxic condition neither with respect to control conditions nor with respect to the level induced by CGS 21680.

Figure 14:
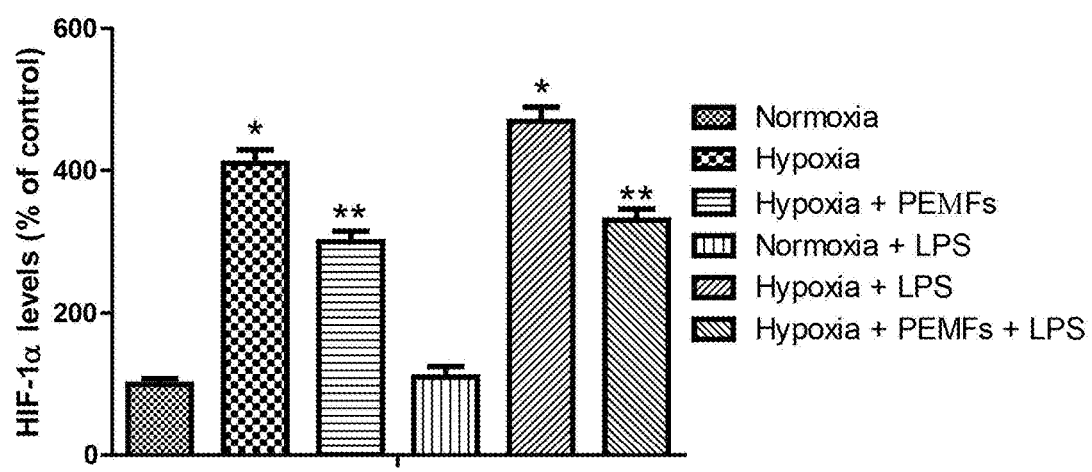
FIG. 14 shows a histogram with results relating to HIF-1α activation in PC12 cells after 4 hours of incubation with LPS (1 μg/ml) and/or PEMFs.

FIG. 14 reports the HIF-1α activation after 4 hours of incubation with LPS (1 μg/ml) and/or PEMFs in normoxic or hypoxic conditions. As expected, under hypoxic conditions a 4-fold of increase of HIF-1α levels was found with respect to control conditions. In these experimental conditions LPS in normoxia or hypoxia did not modify HIF-1α activation. PEMF treatment mediates a significant reduction of HIF-1α expression (25% respect to hypoxia) suggesting a partial recovery versus the normoxic condition.

In conclusion these results show a direct effect of PEMFs on dead cells and a significant increase of cell viability. In addition, an effect of PEMFs on the decrease of HIF-1α levels mediated by hypoxic conditions has been reported.

Taken together, these results show that PEMFs can modify the expression of the HIF-1α gene and act on the mechanisms of neuronal cell death at the basis of ischemic stroke. In particular, PEMFs have the effect of activating the HIF-1α gene, which is connected to apoptosis, in cells subjected to hypoxia.

It is therefore shown that PEMFs reduce apoptosis of neuronal cells in the areas of the brain directly involved by the ischemic stroke through expression of the HIF gene, as well as controlling inflammation of the surrounding tissue mainly through mechanisms mediated by the adenosine A2A receptor.

An early feasibility study was carried out on humans to evaluate safety of the treatment with electromagnetic fields on ischemic stroke patients. Parameters for application in humans were selected on the basis of data from preclinical studies. The study was approved by the Italian Ministry of Health and registered on the website ClinicalTrials.gov (identifier NCT01941147). The study was designed on the basis of the dose-escalation principle, which aims at ensuring safety upon exposure. In this preliminary phase, the treatment was shown to be safe and positive effects were observed both in clinical and in neuroradiological terms.

A phase II clinical trial was designed to obtain data on the effects of the treatment on the ischemic area of patients. Six patients who had experienced an ischemic stroke were divided into two groups. The first group of patients was treated with PEMFs for 45 minutes/day for 5 days starting from 24 hours after stroke. The second group of patients was treated with PEMFs for 2 hours/day for 5 days starting from 24 hours after stroke.

NMR images of the patients' brains were collected in the acute phase, i.e. just after the occurrence of the stroke, and after 30 days from the ischemic event following PEMF treatment. Images taken along the coronal plane and the transversal plane allowed to determine the size and the depth with respect to the skin surface. A simulation of the generation of an electromagnetic field directed to the ischemic area allows to select the kind of solenoid to be used and the parameters that need to be set in order to obtain values of 1.2-1.8 mTesla. The volume of cerebral tissue involved in the ischemic stroke was measured by NMR and is reported in Table 1.

TABLE 1

| Patient | Time of treatment | Pre-PEMF volume of cerebral tissue damaged by stroke (cm$^3$) | Post-PEMF (after 30 days) volume of cerebral tissue damaged by stroke (cm$^3$) |
| --- | --- | --- | --- |
| #1 | 45 minutes | 7.1 | 27.6 |
| #2 | 45 minutes | 1.76 | 1.39 |
| #3 | 45 minutes | 11.8 | 16 |
| Average value | | 6.9 | 15.0 |
| #4 | 2 hours | 25.83 | 23.15 |
| #5 | 2 hours | 2.51 | 1.65 |
| #6 | 2 hours | 5.85 | 3.12 |
| Average value | | 11.4 | 9.3 |

These results show that there is a dose-response relation: a treatment of 45 minutes with PEMFs does not reduce the volume of cerebral tissue damaged by the ischemic stroke after 30 days, whereas a treatment of 2 hours significantly reduces the volume of cerebral tissue damaged by the ischemic stroke after 30 days. These results show that PEMFs represent the first effective non-pharmacological treatment for cerebral ischemic stroke.

What is claimed is:

1. A method for treatment of cerebral ischemic stroke in a subject in need thereof comprising:
   (a) identifying an ischemic area of a brain of the subject; and
   (b) applying an effective electromagnetic field to the ischemic area of the brain by flowing a pulsed current in a solenoid with a pulse duration of 1.3 ms and a frequency of 75 Hz, wherein the pulse current is generated by increasing the current in a linear manner for the entire pulse duration, wherein the electromagnetic field is effective to reduce local edema, to increase neuronal survival or to reduce neuronal apoptosis, relative to a subject that has suffered a stroke but to whom the effective electromagnetic field was not applied, and wherein the electromagnetic field is applied to the ischemic area of the brain for a time of about 2 hours per day for 5 days starting from about 24 hours after occurrence of the cerebral ischemic stroke.

2. The method of claim 1 wherein, in step (a), the ischemic area is identified by nuclear magnetic resonance or computed axial tomography.

3. The method of claim 1 wherein, in step (b), the electromagnetic field applied to the ischemic area of the brain has a value from 1 to 3 mTesla.

4. The method of claim 3, wherein, in step (b), the electromagnetic field applied to the ischemic area of the brain has a value from 1.2 to 1.8 mTesla.

5. The method of claim 1, wherein the subject is human.

6. The method of claim 1, wherein the solenoid is an inductively coupled solenoid.

7. The method of claim 1, wherein the electromagnetic field applied to the ischemic area has a peak intensity of magnetic field of 1.3 to 1.7 mTesla and a corresponding peak amplitude of induced electric voltage of 1.5 to 2.5 mV.

* * * * *